(12) United States Patent
Sengoku

(10) Patent No.: US 6,713,299 B1
(45) Date of Patent: Mar. 30, 2004

(54) APPARATUS FOR SEPARATING BIOLOGICAL MATERIALS

(75) Inventor: Eiichi Sengoku, Rochester, NY (US)

(73) Assignee: Sigma-Aldrich Co., St. Louis, MO (US)

( * ) Notice: Subject to any disclaimer, the term of this patent is extended or adjusted under 35 U.S.C. 154(b) by 0 days.

(21) Appl. No.: 09/613,851

(22) Filed: Jul. 11, 2000

Related U.S. Application Data
(60) Provisional application No. 60/144,540, filed on Jul. 16, 1999.

(51) Int. Cl.[7] .............. C12Q 1/68; C12M 1/12; C12M 1/34
(52) U.S. Cl. .............. 435/288.6; 435/4; 435/6; 435/7.1; 435/287.2; 435/287.3; 435/304.1; 210/263; 210/294; 210/295; 210/198.1; 210/435
(58) Field of Search ............ 435/4, 6, 7.1, 287.2, 435/288.6, 287.3, 304.1; 210/263, 294, 295, 198.1, 435

(56) References Cited

U.S. PATENT DOCUMENTS

| | | |
|---|---|---|
| 4,415,449 A | 11/1983 | Hein |
| 4,419,093 A * | 12/1983 | Deaton et al. ............ 604/46 |
| 4,576,917 A | 3/1986 | Schabron |
| 4,673,501 A | 6/1987 | Wells et al. |
| 4,810,471 A | 3/1989 | Wachob et al. |
| 5,346,999 A | 9/1994 | Cathcart et al. |
| 5,711,917 A | 1/1998 | Juranas et al. |
| 5,725,763 A | 3/1998 | Bonhomme et al. |
| 5,777,098 A | 7/1998 | Gray et al. |
| 5,820,824 A | 10/1998 | Tanaka |
| 5,824,224 A | 10/1998 | Fujishiro et al. |

OTHER PUBLICATIONS

Product Brochure from Varian Associates, Inc. Website "Vac Elut Vacuum Manifolds" pp. 1–9 (Jul. 1998).

* cited by examiner

Primary Examiner—Carla J. Myers
(74) Attorney, Agent, or Firm—Senniger, Powers, Leavitt & Roedel

(57) ABSTRACT

A method and apparatus are provided for the separation of biological materials from one another. The device includes a separation column that is in flow communication with a collection chamber in a reservoir that includes a collection container and a lid. The separation column is mounted on the lid. The collection container includes a concentration zone at the bottom and the container is adapted for use in further separation steps including centrifuging. The device includes a connector that is in flow communication with the collection chamber and is adapted for connecting it to a source of vacuum to help induce flow of liquid through the separation column.

16 Claims, 2 Drawing Sheets

APPARATUS FOR SEPARATING BIOLOGICAL MATERIALS

REFERENCE TO RELATED APPLICATIONS

This application is a non-provisional application claiming priority from provisional application serial No. 60/144,540 filed Jul. 16, 1999.

BACKGROUND OF THE INVENTION

The present invention relates to a device for separating desired biological material(s) from a mixture of biological materials that are in solution or suspended in a liquid. In the past, many devices have been developed to separate mixtures of biological materials from one another. Such biological materials include, DNA, DNA segments, proteins, nucleic acids, other cellular components etc. The separation can be done on the basis of molecular size, molecular weight, affinity for attraction to various filter materials, e.g., adsorptive capacity, etc.

To achieve separation, the materials are preferably dissolved in a solvent to form a solution and the solution is then passed through a separation column as is known in the art. The packing (filter material) in the column and various chemicals that can be added to the column will determine what is collected in the column and what passes through the column to form an eluate that is collected. For example, the column and process can allow small molecules to be separated out in the column and the large molecules to pass through as an eluate. Conversely, the large molecules could be collected in the column and the small molecules could pass through the column in the eluate to be collected for further processing. These separation techniques are well known in the art and the general techniques are described in *Molecular Cloning: A Laboratory Manual* 2nd ed. Vol's 1, 2 and 3 by J. Sambrook, E. F., Fritsch and T. Maniatis, published by Cold Spring Harbor Laboratory, 1989 which are incorporated herein by reference.

The devices used in such processes are generally complicated in structure and operation. One such device is described in U.S. Pat. No. 5,824,224 and is usable to extract and purify DNA. This device handles multiple samples simultaneously and is complicated in structure and operation requiring that the various solutions pass through several stages and containers. For example, the disclosed device uses a plurality of eluate collection chambers requiring a separate housing to apply the vacuum simultaneously to the collection chambers. Such an apparatus is not adapted for effective use when a small quantity of samples or a single sample needs to be processed.

U.S. Pat. No. 5,725,763 describes a simpler filter device that utilizes vacuum to induce a liquid to flow thru a side inlet from a storage container thru a filter to a collection container. The relatively short filter housing sits on top of the collection container with a seal therebetween and appears to be held in place by vacuum. The collection container appears to be a standard small mouth container of substantial volume and further appears to be adapted solely for collection and storage. Further, the connection between the container and the filter is not secure and therefore, there is a risk that the device could be unstable in operation.

The present invention provides an improved and simpler device and method for separating biological materials from one another and is capable of using standard separation columns and techniques. The invention includes a separation column connected in flow communication with a reservoir having a collection chamber adapted for collection of filtrate or eluate. The container containing eluate that is not of interest can be discarded and a clean container installed to collect the next eluate or filtrate. This simplifies the overall separation process and reduces expense and the risk of contamination. The reservoir can also include a concentration zone at the bottom of the collection chamber. The concentration zone has a small volume to height ratio at the bottom of the concentration zone to assist in separating the eluate or filtrate into liquid and solid portions in a centrifuge. The concentration zone is particularly useful when the eluate contains only a small percentage of solid material. A vacuum source is connected to the device to induce flow of liquid thru the separation column and into the reservoir. The invention is also adapted for processing a single sample easily, effectively and economically. The simplicity of the inventive device reduces cost allowing the device to be disposed of after use. Disposability eliminates the need for subsequent equipment clean up and clean up costs.

SUMMARY OF THE INVENTION

Among the several objects and features of the present invention may be noted the provision of a device and method that are used to separate a mixture of biological materials and capture the desired biological material for further processing and use; the provision of a method that is effective and economical in separating biological materials; the provision of such a method that reduces clean up after practice, the provision of such a method that can be used on a wide variety of materials; the provision of such a device that is simple in construction and inexpensive to manufacture; the provision of such a device that can be disposed of after use; the provision of such a device that includes a collection container that can be used in the collection of eluate and in subsequent separation steps like centrifugation; the provision of such a device that uses a pressure differential to induce flow of liquid through the separation column into a reservoir for collection in a collection chamber; and the provision of such a device that is simple in construction and effective in operation requiring minimal component parts.

One aspect of the present invention involves the provision of a separation device for separating biological materials. The device includes a reservoir comprising a container and a lid removably secured to the container. The container defines a liquid collection chamber and has an interior bottom surface forming a concentration zone at the bottom of the collection chamber for collecting solids. The concentration zone has a transverse cross sectional area that increases in size from the bottom of the concentration zone to the top of the concentration zone. A first connector is in fluid flow communication with the collection chamber and is adapted for connection to a vacuum source. A separation column is operatively associated with the reservoir and is in fluid flow communication with the collection chamber. The separation column contains packing material operable to separate mixed biological materials. The column has an inlet and an outlet whereby in operation, liquid containing biological materials to be separated is introduced into the column thru the inlet with a portion of the biological material being retained in the column and a portion of the biological material passes thru the column with the liquid and out the outlet for collection in the collection chamber.

The present also involves the provision of a method of separating biological materials from a mixture of biological materials. The method includes preparing a mixture of liquid and biological materials. A portion of the liquid mixture is introduced into a separation column. Flow of a portion of the introduced liquid mixture is induced through the column with the column allowing a portion of the liquid mixture to pass through the separation column. A portion of the liquid mixture passing through the separation column is collected in a collection chamber of a container with the collection chamber having a concave concentration zone in a bottom portion of the chamber. The container with the collected portion of the liquid mixture therein is placed in a centrifuge. The thus collected portion of the liquid mixture is centrifuged in the container whereby certain biological material contained in the liquid is concentrated and collected in the concentration zone. The concentrated biological material is separated from a major portion of the liquid.

Another aspect of the invention includes a method of separating nucleic acids. The method includes making a solution of nucleic acids and solvent. The solution is placed in a separation column having an inlet and an outlet. A vacuum is applied to the column whereby there is a lower pressure at the outlet than at the inlet thereby inducing flow of a portion of the solution out of the column through the outlet to provide a first eluate and the column retains a portion of the nucleic acids. The first eluate is collected in a container and is then removed from the container. A liquid is introduced into the column to render the retained nucleic acids in the column to a flowable condition in the column. A vacuum is applied to the column to induce the retained nucleic acids and liquid to flow out of the column into the container for collection thereof as a second eluate. The second eluate is centrifuged to concentrate at least a portion of the nucleic acids in the second eluate and the concentrated nucleic acids are collected in a concave concentration zone of the container. A major portion of the liquid in the second eluate is separated from the concentrated nucleic acid material and the separated and concentrated nucleic acid material is recovered.

A further aspect of the invention includes the provision of a separation device for separating materials suspended in liquid. The device includes a reservoir comprising a container and a lid removably secured to the container with the container and lid defining an enclosed liquid collection chamber. A first connector is in fluid flow communication with the collection chamber and adapted for connection to a vacuum source. A separation column is mounted on the lid and is in fluid flow communication with the collection chamber. The separation column contains packing material that is operable to separate mixed materials in a liquid. The separation column has an inlet and an outlet whereby in operation, liquid containing materials to be separated is introduced into the column thru the inlet with a portion of the materials being retained in the column and a portion of the materials passing thru the column with the liquid and out the outlet for collection in the collection chamber.

Other objects and features will be in part apparent and in part pointed out hereinafter.

BRIEF DESCRIPTION OF THE DRAWINGS

Corresponding reference characters indicate corresponding parts throughout the several views of the drawings.

DETAILED DESCRIPTION

Figure 1:
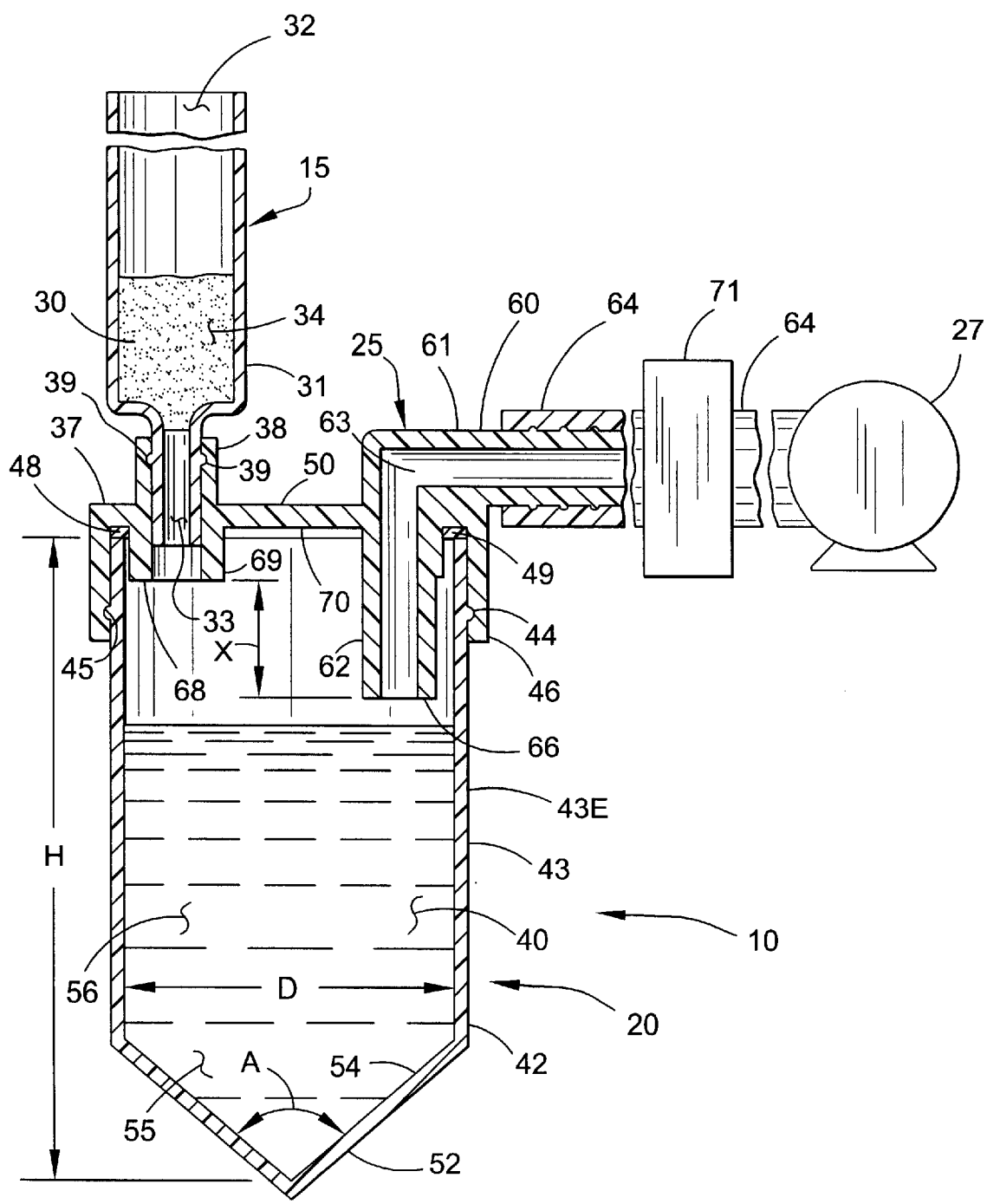
FIG. 1 is a vertical section of the separation device schematically illustrating connection of the device to a source of vacuum.
Figure 2:
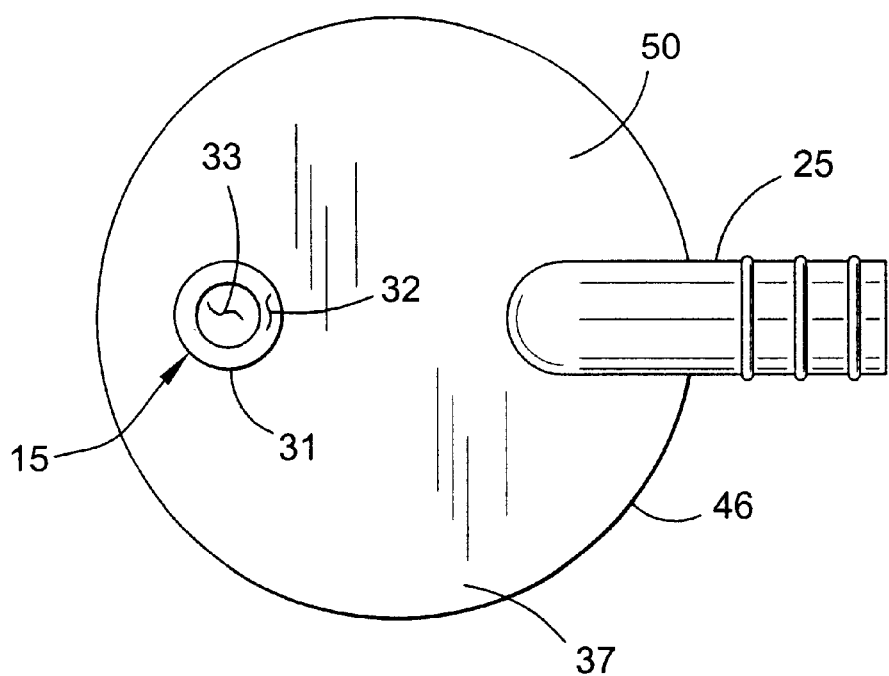
FIG. 2 is a plan view of the separation device.

A separation device designated generally as 10 includes a separation column 15, a reservoir 20 in flow communication with the column and means 25 to connect the reservoir 20 to a source 27 of vacuum.

The column 15 can be of any suitable type for the materials to be separated. Such columns include the types of solid phase extraction with glass fiber membrane columns available from Nalge-Nunc, solid resin (such as silica and derived silica) packed column available from Supelco and silica gel columns from J. T. Baker. The solid phase extraction (SPE) column type using silica resin from Supelco is particularly adapted for the separation of DNA segments. Separation columns can operate on one of several principles. One mode of operation is that the material to be separated has a binding affinity for the packing material 30 such as silica resins or silica membranes. One form of affinity that will achieve separation is by the adsorptive capacity of the packing material for the various materials to be separated. The packing has a preferential ability to attract some materials over others as is known in the art. The separation can also be physical, e.g., by material being adsorbed into pores in particles of the packing material 30 while other material passes through the column 15. The DNA or other biological material can also be physically adsorbed onto the solid phase of the packing material. It is to be understood that the device 10 can be used to separate other than biological materials.

The column 15 has a tubular portion 31 in which the packing material 30 is contained and has an inlet 32 and an outlet 33 at opposite ends of the tubular portion 3. The inlet 32, in a preferred form of device 10, is generally upwardly opening and positioned generally vertically above the outlet 33 in use and the liquid flows in a generally vertical flow path from inlet 32 thru outlet 33. Preferably the tubular portion 31 is made of a polymeric material such as polypropylene, polycarbonate, polyethylene, etc. The dimensions of such columns for the separation of biological materials include a height in the range of between about 2 cm and about 30 cm and preferably in the range of between about 5 cm and about 20 cm. The inside diameter for the tubular section 31 is in the range of between about 0.5 cm and about 10 cm and preferably in the range of between about 2 cm and about 3 cm. The packing material 30 fills a substantial portion of the height of the column 15 as measured from the bottom of the packing material to the inlet 32, e.g. 10% or more and preferably in the range of between about 10% and about 25%.

The column 15 is suitably secured to or mounted on a lid 37 which is part of the reservoir 20. As shown, the column 15 has a lower end adjacent the outlet 33 extending through a fitting 38 through the lid 37. Any suitable securement can be used, e.g., a friction fit between the column 15 and the fitting 38. A preferred securement is a lever lock 39 removably securing the column 15 to the fitting 38 and thus removably mounting the column 15 on the lid 37. The column 15 is thus in fluid flow communication with a collection chamber 40 of the reservoir 20 whereby liquid passing through the column 15 will flow into the collection chamber 40 for collection and further processing. As shown, the column 15 and its inlet 32 are positioned above the collection chamber 40 and the longitudinal axis of the column 15 and the longitudinal axis of the collection chamber 40 are generally parallel.

The reservoir 20 includes a container 42 that defines the collection chamber 40 therein. As shown in FIG. 1, the container 42 has a sidewall 43 with an upper end 44. The sidewall 43 preferably has generally cylindrical interior and exterior surfaces 43I, 43E respectively with the interior surface 43I defining a generally cylindrical upper chamber portion 56. The reservoir 20 also includes the lid 37 that is removably secured to the container 42 whereby the collection chamber 40 is enclosed within the reservoir. A preferred form of securement of the container 42 to the lid 37 is by a frictional engagement between the inside surface of the depending flange 46 and the upper portion of the exterior surface 43E. The flange 46 is annular and preferably an integral part of the lid 37. Other forms of securement can be used such as mechanical interlocking between the lid 37 and container 42 as for example by threaded interengagement and as shown, the securement is by snap lock interengagement. The container 42 has a peripheral rib 44 on the exterior surface 43E at the upper end 44 of the container. The lid 37 includes a peripheral groove 45 in a depending annular flange 46. The rib 44 and groove 45 interengage to secure the lid 37 to container 42. A suitable seal member 48 can be positioned between the top end 49 of the sidewall 43 and the planar top portion 50 of the lid 37. The seal member 48 seals the lid 37 to the container 42 to prevent or reduce vacuum leakage therebetween. The lid 37 and container 42 define an enclosed collection chamber 40. The collection chamber 40 is thus enclosed and separate from the environment surrounding the device 10 except for communication thru the inlet 32 and the means 25.

The collection container 42 has a bottom compartment 52. The bottom compartment 52 has an inside surface 54 that defines a concentration zone 55. The concentration zone 55 is shaped to provide a lower volume per unit of height at the bottom of the bottom compartment 52 (and concentration zone 55) than at the top of the bottom compartment (and concentration zone 55). The concentration zone 55 also preferably has a transverse cross sectional area that generally increases in size from the bottom of the concentration zone to the top of the concentration zone thus helping agglomerate solid material therein and to provide the changing volume per unit of height. Preferably, the concentration zone 55 is concave, more specifically preferably conical, relative to the inside of the container 42. The concentration zone 55 has a small volume to height ratio. In some concave shapes, like conical or hemispherical, the volume to height ratio increases with increasing elevation, i.e., a non-linear relationship, in the concentration zone 55. For example, if the concentration zone 55 is conical with an included angle for the bottom surface of 90° and assuming the height of the concentration zone is 3 units, the volume to height ratio at an elevation of one unit from the bottom is about 1, while at an elevation of 2 units, the volume to height ratio is about 4 while at an elevation of 3 units (the top), the volume to height ratio is about 9. The ratio follows an exponential growth curve, i.e. in the case of a cone, a square growth curve. These ratios can be treated as unitless although, the units would be in area terms, i.e., a length squared term. In use of the device 10, the amount of material to be collected in the bottom compartment 52 can vary significantly depending on the nature of the starting materials. In many cases the amount of separated solid material can be small. By having a small volume to height ratio, recovery of small quantities of separated solid materials is facilitated. Also, by having the volume to height ratio change with height (i.e. increase with height from the bottom of the concentration zone 55), the collection of larger quantities of solids can also be facilitated. Thus, the separation device has a broad range of applicability for mixtures with varying levels of biological material in the liquid. The concentration zone 55 is preferably located generally centrally about and is coaxial with the longitudinal axis of the chamber 40. A preferred shape of the concentration zone 55 is conical although other shapes such as hemispherical can be used. If conical, the included angle A of the surface 54 is in the range of between about 20° and about 120°.

The volume of the collection chamber 40, including the volume of the concentration zone 55 is in the range of between about 25 ml and about 75 ml, preferably in the range of between about 40 ml and about 60 ml and most preferably about 50 ml. The volume of the concentration zone 55 is less than about 10 ml, preferably less than about 7 ml and most preferably about 5 ml. The chamber 40 has an upper chamber portion 56, i.e., that portion above the concentration zone 55. The ratio of the volume of the upper chamber 56 to the volume of the concentration zone 55 is in the range of between about 15:1 and about 3:1, preferably in the range of between about 10:1 and about 5:1 and most preferably in the range of between about 10:1 to about 7:1. The overall inside height H (as measured from the bottom of the concentration zone 55 to the top of the container 42) of the container 42 is in the range of between about 5 cm and about 15 cm, preferably in the range of between about 7 cm and about 12 cm and most preferably in the range of between about 10 cm and about 12 cm. The inside diameter D of the upper chamber 56 (in the cylindrical section) is in the range of between about 1.5 cm and about 4.5 cm, preferably in the range of between about 2 cm and about 3.3 cm and most preferably in the range of between about 2.3 cm and about 2.5 cm.

The device 10 also includes the means 25 adapted for connecting the chamber 40, and hence the concentration zone 55 and upper chamber 56, in flow communication to the source 27 of vacuum. As can be seen in FIG. 1, when the device 10 is assembled for use, the column 15, the chamber 40, the means 25 and the vacuum source 27 are in fluid flow communication with one another. The chamber 40 is enclosed and sealed from the exterior of the reservoir 20 and is in flow communication with the environment thru the inlet 32. The application of vacuum to the device 10 causes a pressure differential between the inlet 32 (high pressure end) and outlet 33 (low pressure end) causing liquid to flow in the direction from the inlet 32 to the outlet 33. The collection chamber 40 has a lower pressure than its exterior, the outlet 33 and the column 15 and flow of liquid into the chamber 40 from the column 15 is thereby induced by the pressure differential in addition to gravity induced flow.

As shown in FIG. 1, the means 25 includes an L-shaped elbow 60 having two tubular portions 61, 62. The elbow 60 is secured to or mounted on the lid 37 in any suitable manner. For example, the elbow 60 can extend through an aperture in the top portion 50 of the lid 37. The securement can be by a tapered friction fit or alternatively, the securement can be by adhering or otherwise securing the elbow 60 to the lid 37. Preferably, and as shown, the elbow 60 is an integral part of the lid 37. The elbow 60 has a flow passage 63 therein that is in flow communication with the chamber 40 when the lid 37 is on the container 42. The elbow 60 has an inlet end 66 positioned in the collection chamber 40. The fitting 38 has an outlet end 68 at its lower end. It is to be understood that the outlet end 68 could be flush with an inside surface 70 of the lid 37 and still be in the collection chamber 40. As seen in FIG. 1, the inlet end 66 is at an elevation lower than the elevation of the outlet end 68 relative to the bottom of the collection chamber 40. The outlet end 68 is spaced above the level of the inlet end 66 a distance X of at least about 5 mm and preferably at least about 10 mm. By having the outlet 68 at a level higher than the inlet 66 the liquid level in the collection chamber 40 cannot rise to the outlet 68 and thus avoids contact of the liquid with the exterior 69 of the fitting 38 reducing the risk of contamination and the need to clean the exterior 69. A conduit 64 connects the elbow 60 and thus the collection chamber 40 and the column 15 inflow communication with the source 27 of vacuum. A liquid trap, shown schematically as 71, can be connected in flow communication between the means 25 and the source 27 preferably in the conduit 64. Any liquid that would rise to the inlet 66 would be collected or trapped in the trap 71 for subsequent disposal. The source 27 ultimately exhausts to the environment or exterior of the container 42. Preferably, the vacuum pressure in the chamber 40 during operation is in the range of between about 5" Hg and about 25" Hg.

It is preferred that the lid 37, container 42 and elbow 60 be made of a polymeric material such as polypropylene, polystyrene, polycarbonate, etc. It is also preferred that the container 42 be transparent or semitransparent.

The separation device 10 is operated as follows. The process is described in terms of a mixture of biological materials that are in solution in a solvent. However, it is to be understood that a mixture can also be formed of biological materials or other solid materials to be separated and a suitable liquid and not in solution and still be separated in the device 10. The solid materials can include a mixture of various biological materials. The liquid can be a solvent to one or more of the solid materials. Solvent for biological materials can include aqueous solutions including chaotropic salt solutions and mixtures of those solvents. A particularly effective aqueous salt solution for DNA includes aqueous guanidine hydrochloride. Alcohols such as ethanol and isopropanol can also be included in the solvent. A mixture such as a solution is formed of a mixture of biological materials and a suitable liquid such as a solvent. When the biological materials are in solution, the various molecules will be freed from one another for subsequent separation. The biological materials can include proteins, nucleic acids, DNA, DNA fragments and other cellular components. The molecular weights of such biological materials are in a distribution range of very small molecules to molecules of genomic DNA that are hundreds of KB's long. A column 15 is chosen that will effect the desired separation of biological materials contained in the mixture of biological materials. The process for operating the selected column 15 to achieve the desired separation is also selected. For example, the column 15 could separate the molecules of biological material on the basis of molecular weight or size, or on the basis of the molecules' affinity and lack of affinity for the packing material as is well known in the art.

The column 15 is mounted on the lid 37 and the container 42 is secured to the lid 37. The device 10 is mounted in a holder such as a clamp on a stand. The source 27 of vacuum is then connected to the elbow 60 and a vacuum is applied to the chamber 40 and column 15. The mixture of the biological materials and liquid is introduced into the column 15 at the inlet 32. The mixture flows through the column 15 with a portion of the biological material and liquid being retained or captured in the column 15 and a portion being captured in the collection chamber 40. If the desired biological material is in the column, further processing of the desired biological material is conducted to remove it from the column 15. In this case the collected first eluate or filtrate is discharged from the chamber 40 such as by removing the container 42 from the lid 37 and pouring out the contents. If needed, the chamber 40 is suitably cleaned and the container 42 is reattached to the lid 37. Additional suitable solvent and/or other suitable chemicals are introduced into the column 15 to render the retained biological material flowable for removing the desired biological material from the column 15. The new mixture of liquid and biological material is discharged from the column 15 and collected in the collection chamber 40 forming a second eluate or filtrate. This process of selectively removing biological material is repeated until the desired biological material and liquid are contained in a chamber 40. Prior to collection of the desired biological material, a new container 42 can be mounted on the lid 37 to insure a non contaminated container for collecting the desired material. When the desired or target biological material and liquid are in the chamber 40, it is ready for further processing.

If the liquid and target biological material in the chamber 40 is ready for centrifuging separation, the container 42 can be placed in the centrifuge at that time. Alternatively, the eluate can be transferred to a vessel typically used to hold a sample in a centrifuge. However, some mixtures (including solutions) of biological material will need further treatment before centrifuging, as is known in the art. For example, a solution may need to have precipitating chemical(s) added to precipitate the desired biological materials out of solution. When the mixture is ready for separation, the mixture is placed in the centrifuge in the container 42. The container and biological material(s) therein are appropriately centrifuged to obtain the desired separation of the solids from the liquid with the solids collecting in the concentration zone 55. Centrifugation can include forces above about 5000 g's. The liquid above the solids is then suitably removed from the container 42 such as by decanting. This leaves the solids separated from a substantial portion or majority of the liquid. The solids will have some residual liquid present which can be at least partially removed to the desired level as is known in the art, e.g., by drying. The drying temperature and time should be below that which would denature the biological material. The drying is carried out at any suitable temperature and can be from room temperature (approximately 20° C.) to a higher temperature (depending on the liquid fraction) for a period of time sufficient to achieve the desired level of dryness. The centrifuging is carried out under a force adequate to achieve the desired separation as is known in the art.

EXAMPLE

E. coli is harvested by pelleting 250–500 ml through centrifuging a mixture of E. coli and liquid at ≧4,000 for 10 minutes. The supernatant is discarded. 22 ml of Solution 1 and 20 µl of Rnase A are added to the E. coli to form a suspension. The bacterial pellet is completely resuspended by pipetting the cells in solution (Solution 2). The solution is homogeneous.

Lyse the resuspended cells by adding 22 ml of Solution 2 to a tube containing resuspended cells. The contents of the tube were gently mixed until the mixture started to clear. Lysis should not exceed about 5 minutes since prolonged alkaline lysis may permanently denature supercoiled BAC/PAC/P1 DNA. The cell debris was precipitated by adding 44 ml of Solution 3. The mixture was immediately mixed in the tube about ten times via gentle inversion of the tube. A crude lysate was produced. The cell debris was pelleted by centrifuging at ≧9000 g's for 15 minutes.

The liquid fraction from the centrifuging was added to a column 15 of the device 10 and vacuum was applied. The added liquid was kept at a level above the top of the packing. All the lysate was allowed to flow through the column. 50 ml of Solution 4 was then added to the column 15 to wash the column and the vacuum was allowed to be applied for 5 minutes after solution 4 passed through the column to remove excess ethanol. A new container 42 was attached to the lid 37. 6 ml of solution 1 was added to the column 3 times and collected in the chamber 40. 15 μl of LPA (linear polyacrylamide), 1.8 ml of 3M sodium acetate pH 5.3 and 45 ml of 95–100% ethanol were added to the eluate. The container and its contents were gently mixed. The resultant mixture was then placed into centrifuge tubes and centrifuged at ≧10,000 g's for 10 minutes. The supernatant was discarded. The pelleted DNA was washed with 10 ml of 70% ethanol and the supernatant discarded. The DNA was dried under vacuum.

Solution 1 is a mixture of 100×Tris-EDTA Buffer with a pH of 8.0 with water in an amount where the aqueous solution concentration of the buffer is 1×(10 mm Tris 1 mm EDTA). Solution 2 is a mixture of water, 10% Lauryl Sulfate (SDS) and 1 N NaOH where the final concentration is 1% Lauryl Sulfate and 0.2 N NaOH. Solution 3 is a mixture of water, Guanidine Hydrochloride, Potassium Acetate, Acetic Acid glacial and water where the final aqueous solution concentration includes 4M of Guanidine Hydrochloride and 1M(pH 5.0) of Potassium Acetate. Solution 4 is a mixture of 1M TrisHCl (pH 7.6), 5M Sodium Chloride and water. The final aqueous solution concentration includes includes 0.05 M of Tris-HCl and 1M of Sodium Chloride.

The device 10 does not require the use of a second chamber to apply the vacuum. The device 10 is self contained and the vacuum is applied directly to the collection chamber 40 which is enclosed and defined by the container 42 and lid 37 thus eliminating the need for a separate vacuum chamber. This results in a pressure differential between the chamber 40 and the exterior of the device 10 during operation of the device. Such a structure is adapted for one time usage and subsequent disposal. Further, the device 10 can use any type column 15 since it is removably mounted on the lid 37 allowing for a variety of different separation processes with various types of materials to be separated.

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

As various changes could be made in the above constructions without departing from the scope of the invention, it is intended that all matter contained in the above description or shown in the accompanying drawings shall be interpreted as illustrative and not in a limiting sense.

What is claimed is:

1. A separation device for separating biological materials, said device comprising:
   a reservoir comprising a container and a removable lid covering an upper portion of the container, said container defining a liquid collection chamber, said container having an interior bottom surface forming a concentration zone at the bottom of the collection chamber for collecting solids, said concentration zone having a transverse cross sectional area that increases in size from a bottom of the concentration zone to a top of the concentration zone;
   a first connector in fluid flow communication with the collection chamber and adapted for connection to a vacuum source;
   a separation column having an outlet in fluid flow communication with the collection chamber, said separation column containing packing material operable to separate mixed biological materials, said separation column also having an inlet whereby in operation, liquid containing biological materials to be separated is introduced into the column thru the inlet with a portion of the biological material being retained in the column and a portion of the biological materials passing thru the column with the liquid and out the outlet for collection in the collection chamber.

2. A separation device as set forth in claim 1 wherein said collection chamber has an upper chamber portion above the top of the concentration zone, said upper chamber portion being generally cylindrical and, the concentration zone is concave.

3. A separation device as set forth in claim 2 wherein said collection chamber has a longitudinal axis and said concentration zone is generally coaxial with the longitudinal axis of the chamber.

4. A separation device as set forth in claim 3 including a second connector in fluid flow communication with the collection chamber and adapted for connecting the separation column to the lid.

5. A separation device as set forth in claim 1 wherein the packing material is of a type that will separate the biological material on the basis of molecular weight.

6. A separation device as set forth in claim 1 wherein the packing material is of a type that will separate the biological material on the basis of adsorption affinity of the biological material for the packing material.

7. A separation device as set forth in claim 2 wherein said collection chamber has an inside height in the range of between about 5 cm and about 15 cm and the collection chamber has a generally cylindrical upper chamber portion with an inside diameter in the range of between about 1.5 cm and about 4.5 cm.

8. A separation device as set forth in claim 1 wherein said collection chamber has a volume in the range of between about 25 ml and about 75 ml.

9. A separation device as set forth in claim 2 wherein said upper chamber portion has a volume and said concentration zone has a volume and the ratio of the upper chamber portion volume to the concentration zone volume is in the range of about 15:1 and about 3:1.

10. A separation device as set forth in claim 1 wherein the concentration zone is generally conically shaped.

11. A separation device as set forth in claim 10 wherein the conically shaped concentration zone has an included angle A in the range of about 20° and about 120°.

12. A separation device as set forth in claim 1 wherein the concentration zone has a volume to height ratio that increases exponentially with increasing height from the bottom of the concentration zone.

13. A separation device for separating materials suspended in liquid, said device comprising:
   a reservoir comprising a container and a removable lid covering an upper portion of the container, said container and lid defining a liquid collection chamber having a bottom;
   a connector mounted on said lid and being in fluid flow communication with the collection chamber and adapted for connection to a vacuum source, said connector having an inlet end in said collection chamber and positioned at a first elevation relative to the bottom of the collection chamber;
   a fitting mounted on said lid and being in fluid flow communication with the collection chamber, said fitting having an outlet end in said collection chamber positioned at a second elevation relative to the bottom of the collection chamber, said second elevation being higher than said first elevation by a distance X;

a separation column mounted on said fitting and in fluid flow communication with the collection chamber, said separation column having an inlet and an outlet whereby in operation, liquid containing materials to be separated is introduced into the column thru the column inlet with a portion of the materials being retained in the column and a portion of the materials passing thru the column with the liquid and out the column outlet for collection in the collection chamber.

14. A separation device as set forth in claim 13 wherein the distance X between the first elevation and the second elevation is at least about 5 mm.

15. A separation device as set forth in claim 14 wherein the distance X between the first elevation and the second elevation is at least about 10 mm.

16. A separation device as set forth in claim 13 including:
a vacuum source connected in flow communication with the connector; and
a liquid trap connected in flow communication between the connector and the vacuum source.

* * * * *

UNITED STATES PATENT AND TRADEMARK OFFICE
CERTIFICATE OF CORRECTION

PATENT NO. : 6,713,299 B1
DATED : March 30, 2004
INVENTOR(S) : Eiichi Sengoku

It is certified that error appears in the above-identified patent and that said Letters Patent is hereby corrected as shown below:

<u>Column 4,</u>
Line 50, "lever lock" should read -- leuer lock --.

Signed and Sealed this

Thirty-first Day of August, 2004

JON W. DUDAS
*Director of the United States Patent and Trademark Office*